United States Patent [19]

Edman et al.

[11] Patent Number: 4,798,722

[45] Date of Patent: Jan. 17, 1989

[54] PERMANENT WAVING COMPOSITION

[75] Inventors: Walter W. Edman; Ernest J. Klemm, both of Westport, Conn.

[73] Assignee: Zotos International, Inc., Darien, Conn.

[21] Appl. No.: 929,723

[22] Filed: Nov. 12, 1986

[51] Int. Cl.$^4$ ............................................. A61K 7/09
[52] U.S. Cl. ......................................... 424/72; 424/71
[58] Field of Search ................. 424/71, 72; 514/2, 63; 132/7

[56] References Cited

U.S. PATENT DOCUMENTS

| | | | |
|---|---|---|---|
| 2,479,382 | 8/1949 | Mace | 424/72 |
| 2,688,972 | 9/1954 | Brown | 424/72 X |
| 2,708,940 | 5/1955 | De Mytt et al. | 424/72 X |
| 4,201,235 | 5/1980 | Ciavatta | 132/7 |
| 4,275,748 | 6/1981 | Graziano | 132/7 |
| 4,423,032 | 12/1983 | Abe et al. | 514/63 X |
| 4,459,284 | 7/1984 | Azuma et al. | 424/72 |
| 4,517,175 | 5/1985 | Iwabuchi et al. | 132/7 X |
| 4,529,586 | 7/1985 | De Marco et al. | 514/63 |
| 4,609,750 | 9/1986 | Kollmeirer et al. | 514/63 |
| 4,658,839 | 4/1987 | Dallal et al. | 132/7 |

FOREIGN PATENT DOCUMENTS

| | | | |
|---|---|---|---|
| 3138142 | 4/1983 | Fed. Rep. of Germany | 424/72 |
| 243011 | 12/1985 | Japan | 424/72 |
| 69717 | 4/1986 | Japan | 424/72 |

OTHER PUBLICATIONS

R. S. Burnett, "Proteins in Cosmetics" American Perfumer and Cosmetics, vol. 78, No. 10, 1963, pp. 69–72.

Primary Examiner—Ellis P. Robinson
Assistant Examiner—Susan S. Rucker
Attorney, Agent, or Firm—Mattern, Ware, Stoltz & Fressola

[57] ABSTRACT

A permanent waving composition which imparts to the hair a substantially increased curl retention, as well as substantially improved hair manageability and improved hair feel and appearance, is attained by combining strong hydrogen bonding amino acids with a water soluble or emulsifiable silicone-based compound as additives to the basic permanent wave ingredients. By employing these two additives, a synergistic effect is achieved, with the resulting permanently waved head of hair possessing substantially increased curl retention, ease of manageability, and substantially improved feel and appearance. Preferably, the strong hydrogen bonding amino acids are formed from hydrolyzed silk protein.

17 Claims, No Drawings

PERMANENT WAVING COMPOSITION

TECHNICAL FIELD

This invention relates to the art of permanent waving of hair, and more particularly to novel compositions therfore which impart substantially increased lasting or staying ability to the permanently waved hair.

BACKGROUND ART

In view of the unique composition of hair fibers and the various changes in styles and fashion, the waving of hair has long been of particular interest. In order to best understand the various methods in which hair fibers can be styled or waved, it is important to remember that normal hair has three major bonds that hold the configuration of the hair and are responsible for the strength of the hair. These three bonds are salt linkages, hydrogen bonds, and disulfide bonds.

As is well known, hair is a protein produced from units known as "amino acids". A high proportion of these are diamino and dicarboxylic "amino acids", and thus the hair fiber is amphoteric in character. Since the number of free acid and basic groups are approximately equal, the hair's mechanical properties, such as its strength, is at its maximum at neutrality (pH 7). For example, the fiber becomes easier to stretch as the pH increases or decreases from pH 7. The cohesion of hair is also demonstrated by the minimum swelling in water at neutrality.

Because they are so numerous, the hydrogen bonds, involving the amino hydrogen and carbonyl oxygen of the amide linkages, are most important. Water, particularly in the monomolecular state, as occurs with moisture in the air (humidity), can weaken these bonds, by becoming a part of a hydrogen bonding structure. However, some of these hydrogen bonds are protected by hydrophobic bonds and will remain even when the hair is wet with water. More powerful hydrogen bond breakers, like high concentration of lithium bromide and urea are required for complete breakage of all hydrogen bonds.

As long as the hair fiber is dry, the strength of the hair fiber is not reduced. For example, a straight hair, wet with water and held by mechanical force in a curly configuration while drying will remain in a curly shape due to the formed hydrogen bonds and salt linkages, and it will not return to its straight shape so long as it remains dry. However, unless mechanically restrained, upon being wet with water, the hair will lose its curly configuration and become straight.

Furthermore, when hair is set by the use of water alone, the hair will gradually lose its curly shape through the absorption of atmospheric moisture and the resulting rearrangement of the hydrogen bonds. This is due to the fact that in water, the dominant bond is disulfide bond, while in the dry state, the dominant bonds are the salt linkages and the hydrogen bonds.

In regard to the disulfide bonds, hair is composed of a unique protein material called "keratin", which is distinguished by the fact that it contains a very significant amount of an amino acid (cystine) which contains the element sulfur in addition to the elements nitrogen, oxygen, carbon and hydrogen. In the natural synthesis of hair, the element sulfur covalently links adjacent polypeptide chains (K) through two sulfur atoms (S-S) to give keratin protein (K-S-S-K). Only by chemical action can this covalent linkage be broken.

Similarly, it is well established that in order to permanently wave hair, this disulfide linkage must be broken. In this regard, many prior art compositions have been developed for the "cold permanent waving" of hair. Typically, these prior art systems treat the hair with reducing agent which breaks the disulfide (cystine) linkage in the hair while the hair is wound around a curling rod. These prior art systems are typified by the disclosures in U.S. Pat. Nos. 2,479,382, 2,577,710, 2,577,711, 2,688,972, and 2,708,940.

It is believed that certain hydrogen bonds are protected by the cystine bond and are only broken by water when the cystine bond is split into two cysteine moieties. By the same rationale, these hydrogen bonds are re-formed in the new configuration and protected by the newly formed cystine bonds created in the neutralization step of permanent waving. In effect, these protected hydrogen bonds supplement the disulfide bonds in creating permanency to the new curl configuration.

In general, permanent hair waving is usually carried out by subjecting the hair to reagents containing a free —SH group or thiol. These materials are also called mercaptans. In this treatment, the hair is usually first wound on rollers and the saturated with the thiol. The thiol waving agent acts to break the disulfide bonds within the hair fiber forming thiol groups in the hair protein and disulfide bonds between two thiol waving agent molecules. The chemistry involved in the reaction of the mercaptan with the cystine disulfide bonds in the hair fiber is illustrated by the following chemical equation:

$$KSSK + 2RSH \rightleftharpoons 2KSH + RSSR$$

When a sufficient number of hair disulfide bonds have been broken, the hair is realigned to pair previously unpaired hair protein thiol groups opposite each other. At this point, the hair is rinsed, removing the unreacted thiol waving agent and disulfide reaction product formed from it. Then, the hair is saturated with an oxidizing agent, or neutralizer, such as hydrogen peroxide or bromate salt, to reform disulfide bonds between the newly paired hair protein thiols, thereby giving the hair a new configuration or wave, or adding curl to the hair. By rebonding the sites of the reduced keratin in their new curled configuration, a permanent set which is impervious to water is established.

The rebonding of the reduced sites accomplished by the action of the chemical oxidizing agent is illustrated by the following chemical reaction:

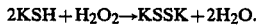

$$2KSH + H_2O_2 \rightarrow KSSK + 2H_2O.$$

In spite of the substantial effort that has occurred in the development of various permanent waving compositions of this general nature, there has been a general inability to improve the holding power or curl configuration retention of "cold permanent waving" formulations. The typical problem encountered with the use of mercaptan reducing agents for the permanent waving of hair is that the permanency of the curl will not last until it is cut off. Instead, the curl relaxes slowly from the normal wear and tear of every day hair care. In this normal grooming process of shampooing, combing, drying and brushing the hair, the fibers are constantly being put under tension and exposed to forces that oppose the new disulfide and hydrogen bonds that were created in the new curl configuration.

In addition to longer curl retention, the industry has also sought to increase the luster, sheen, gloss and manageability of the hair, as well as provide a permanently waved head of hair which is soft, supple, and possesses a natural feel. However, these goals have not been fully attained.

Therefore, it is principal object of the present invention to provide a "cold permanent waving" formulation which imparts to the permanently waved head of hair a substantially increased lasting and curl retention ability.

Another object of the present invention is to provide a "cold permanent waving" formulation having the characteristic features described above which also imparts to the permanently waved head of hair a high luster, gloss, sheen and improved manageability.

Another object of the present invention is to provide a "cold permanent waving" formulation having the characteristic features described above which also imparts to the permanently waved head of hair a full-bodied appearance which is easily managed and feels soft and silky.

Other and more specific objects will in part be obvious and will in part appear hereinafter.

DETAILED DESCRIPTION OF THE INVENTION

The present invention overcomes the prior art limitations and difficulties by combining generally conventional cold permanent waving compositions with two specific hair enhancing additives. These two hair enhancing additives comprise a hydrolyzed silk protein and a water soluble or emulsifiable silicone-based compound.

The incorporation of silk protein in a permanent waving composition is considered to be unique. It has been found that the silk protein contributes substantially to the permanent waving of the hair and is believed to interact with the permanent wave composition to impart to the overall composition a substantially increased curl or wave staying power or long-lasting ability. Furthermore, the increased curl or wave longevity, as well as hair manageability, is further enhanced and substantially improved by combining a water soluble or emulsifiable silicone-based compound therewith.

Although some improvement was found with the separate use of the compounds, an interactive, synergistic result is attained when the water soluble or emulsifiable silicone-based compound is combined with a hydrolyzed silk protein. These constituents, in addition to the generally conventional permanent waving compounds, have produced an overall cold permanent waving formulation which provides both luster, sheen, manageability and soft and silky feeling hair, as well as allowing the head of hair to retain the permanent waved configuration for a substantially increased time period. Now, for the first time, the commonly experienced problem of curl relaxation following the application of a cold permanent wave is substantially eliminated or reduced and a firm and permanent wve is achieved.

Another advantage of the present invention is that the conventional method of permanently waving human hair on the head is employed without deviation. In this way, the present invention is easily employed, without requiring special steps to be learned.

Hydrogen bonds, especially those between an amide nitrogen and an adjacent carbonyl oxygen make a major contribution to the strength of the fiber. Dry fibers are more difficult to elongate than fibers immersed in water. The explanation assumed is that hydrogen bonds are weakened in the presence of water and therefore offer less resistance to the unfolding of polypeptide chains. The magnitude of the contribution of hydrogen bonds to the strength of wet keratin fibers is in the order of about 35%. There is persuasive evidence that hydrogen bonds—not disulfide bonds alone—are involved in present-day hair waving practices. One of the primary objectives of this invention is to increase the percentage of hydrogen bonds in the half fiber, especially those unavailable or resistant to water.

Silk is a protein fiber unique and different from hair or wool in that its composition is high in strong hydrogen bonding amino acids, glycine, alanine, serine and tyrosine and contains practically no sulfur containing cystine. These four amino acids comprise over 80% of the silk fiber and it is their strong hydrogen bond cross linkages that hold the fiber together making it resistant even to boiling water.

Silk can be hydrolyzed to its individual amino acids by acid, alkaline or enzymatic processes. It is commercially available and listed in the CTFA Dictionary as Silk Amino Acids. The hydrolysate contains seventeen amino acids with a mean molecular weight of 90. This means that the molecules are able to penetrate the cuticle in undamaged hair and enter the matrix in the cortex area of the hair fiber.

This invention is based on the discovery that one can substantially improve the permanent waving of hair and extend the period of time that a new wave configuration is retained in the hair by incorporating in the waving lotion some of these strong hydrogen bonding amino acids. The precise nature of this holding action is not completely understood but it is believed that these amino acids are entrapped by the closing of the sulfur bonds in the new wave configuration making additional hydrogen bonds unavailable to water and thus complementing the disulfide bonds in maintaining the permanency of the curl.

This theory is offered only as a possible explanation and is not intended to further limit or define the present invention. It is recognized that other mechanism may contribute to the permanency of the set in the present invention. For example, a layer of a polysiloxane on the hair surface may provide a hydrophobic barrier that reduces the rate of absorption of atmospheric moisture and thus reduces the rate of hydrogen bond rearrangement and loss of permanency.

In addition to the increased staying power, another objective of this invention is to provide increased lubricity to the hair fiber for increased slip. In this way, little or no tension is applied to the hair during the subsequent combing and brushing of a freshly made permanent wave. It is particularly desirable to incorporate this lubricity action in the permanent wave lotion where its actin can be effective when the hair is in a softened and easily stretched condition.

In order to attain this goal, the present invention also incorporates a water soluble or emulsifiable silicone-based compound, in addition to the Silk Amino Acids. In the preferred embodiment, dimethicone copolyol or dimethylsiloxane-glycol copolymer comprises the silicone-based compound. The preferred dimethicone copolyol is nonionic and water soluble, and comprises a polymer of dimethylsiloxane with polyoxyethylene and/or polyoxypropylene side chains. The following represents the general formula for dimethicone copolyol:

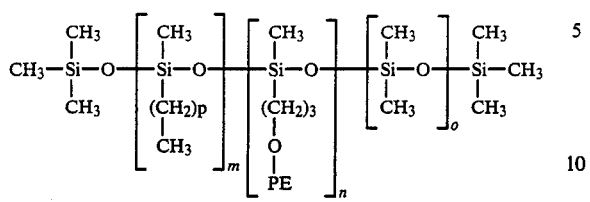

where PE=(C$_2$H$_4$—) x (C$_3$H$_6$O—)yH.

The incorporation of a silicone-based compound provides the hair with lubricity for increased slip and easy combing action. Furthermore, the silicone-based compound provides a synergistic effect, increasing the action of the other constituents used in the hair treatment composition.

Although the use of dimethicone copolyol is preferred, other water soluble or emulsifiable silicone-based compounds can be employed, without departing from the scope of the present invention. One other alternate compound is dimethicone, which is a mixture of fully methylated linear siloxane polymers end blocked with trimethylsiloxy units. Empirically, the formula for dimethicone is (C$_2$H$_6$OSi) x C$_4$H$_{12}$Si, with the following being representative of its general formula:

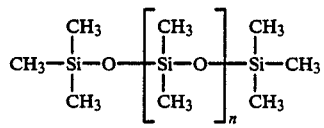

In addition, amodimethicone can be employed as the silicone-based compound. Amodimethicone is a silicone polymer end blocked with amino functional groups. Its formula is represented as follows:

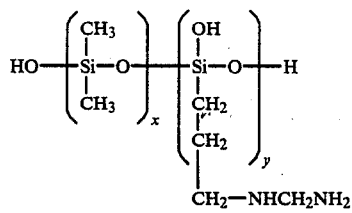

where x has a value of 4 or more

Another silicone compound which can be employed is stearoxytrimethylsilane which is an organo-silicon compound having the empirical formula of C$_{21}$H$_{46}$OSi. Its formula genrally conforms to the following:

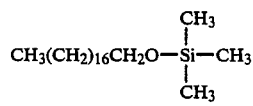

In addition, stearoxy dimethicone can be employed, which is a polymer of dimethylpolysiloxane end blocked with stearoxy groups.

Furthermore, the silicone compound employed in the permanent wave lotion can be a quaternized silicone compound or a betaine silicone compound. A typical quaternized silicone compound is polysiloxane polydimethyl dialkylammonium acetate copolymer, having the following general formula:

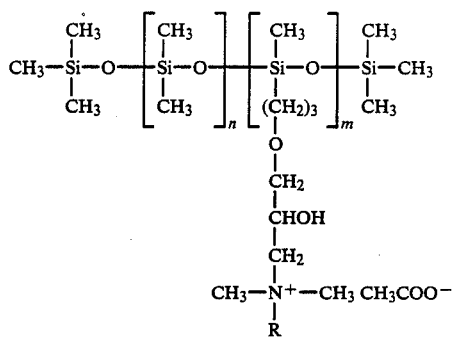

The betaine silicone compounds is typified by polysiloxane polyalkyl betaine copolymer having the following general formula:

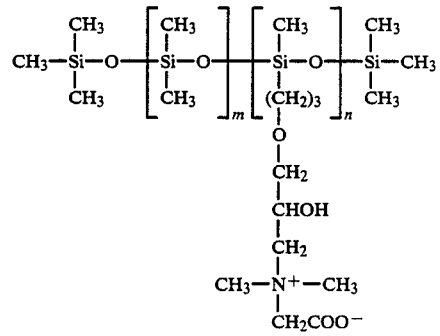

BEST MODE FOR CARRYING OUT THE INVENTION

In order to clearly and precisely define the novel composition we have developed for permanently waving hair with the substantial improvements detailed above, the following examples are presented to teach the best mode for carrying out this invention, as well as provide the proof for the claims we make for this invention.

In Tables I–IV, compositions of four permanent wave lotions made in accordance with this invention are detailed, with the ranges of each constituent clearly indicated therein. It has been found that these four compositions are substantially equivalent in their efficacy, with each composition providing substantially equivalent enhanced curl retention, hair manageability, and hair appearance improvement.

TABLE I

|  | PERCENT BY WGT/VOLUME |
|---|---|
| Ammonium Thioglycolate | 2.0–10.0% |
| Wetting Agent | 0.5–2.0% |
| Hydrolyzed Silk Protein (Silk Amino Acids) | 0.1–2.0% |
| Silicone-Based Compound | 0.1–2.0% |
| Ammonium Dithiodiglycolate | 2.0–10% |
| Water | qs to 100% |

TABLE I-continued

| | PERCENT BY WGT/VOLUME |
|---|---|
| pH adjusted to | 6.0–10.0 |

(pH adjustments may be made with alkanolamines, ammonia or the carbonates of ammonia).

TABLE II

| | PERCENT BY WGT/VOLUME |
|---|---|
| Glyceryl Monothioglycolate | 2.0–30.0% |
| Wetting Agent | 0.5–2.0% |
| Hydrolyzed Silk Protein (Silk Amino Acids) | 0.1–2.0% |
| Silicone-Based Compound | 0.1–2.0% |
| Diglycerol dithiodiglycolate | 2.0–30% |
| Water | qs to 100% |
| pH adjusted to | 6.0–8.5 |

(pH adjustments may be made with alkanolamines, ammonia or the carbonates of ammonia).

TABLE III

| | PERCENT BY WGT/VOLUME |
|---|---|
| Ammonium Thioglycolate | 2.0–10.0% |
| Wetting Agent | 0.5–2.0% |
| Hydrolyzed Silk Protein (Silk Amino Acids) | 0.1–2.0% |
| Silicone-Based Compound | 0.1–2.0% |
| Water | qs to 100% |
| pH adjusted to | 6.0–10.0 |

(pH adjustments may be made with alkanolamines, ammonia or the carbonates of ammonia).

TABLE IV

| | PERCENT BY WGT/VOLUME |
|---|---|
| Glyceryl Monothioglycolate | 2.0–30.0% |
| Wetting Agent | 0.5–2.0% |
| Hydrolyzed Silk Protein (Silk Amino Acids) | 0.1–2.0% |
| Silicone-Based Compound | 0.1–2.0% |
| Water | qs to 100% |
| pH adjusted to | 6.0–8.5 |

(pH adjustments may be made with alkanolamines, ammonia or the carbonates of ammonia).

EXAMPLE I

In order to prove the efficacy of the composition of this invention, the permanent wave lotion composition detailed in Tables V and VI were prepared and the results were compared and analyzed. The composition in Table V represents a typical ammonium thioglycolate permanent wave lotion, while the composition in Table VI defines a substantially similar lotion, except for the incorporation of the enhancing additives of this invention.

TABLE V

| | % BY WGT/VOLUME |
|---|---|
| Ammonium Thioglylcolate | 8.7% |
| Ammonia | 1.2% |
| Wetting Agent | 1.0% |
| Water | qs to 100% |

TABLE VI

| | % BY WGT/VOLUME |
|---|---|
| Ammonium Thioglylcolate | 8.7% |
| Ammonia | 1.2% |
| Wetting Agent | 1.0% |
| Hydrolyzed Silk Protein (Silk Amino Acids) | 1.0% |
| Silicone-Based Compound | 1.0% |
| Water | qs to 100% |

In conducting the comparative tests, both lotion compositions were prepared and tested using two grams of six inch strands of hair for each composition. As detailed herein, the curl permanency was tested using a "racking test", which we have developed and have employed for many years. The hair strands were shampooed and wound on ¼ inch mandrels. Then the hair strands were processed with one of the two waving lotions for a set period of time and, finally, water rinsed and neutralized with a 2.3% hydrogen peroxide solution.

After water rinsing, the hair strands were combed and allowed to fall into a wave pattern without coaxing. The strands were then placed on a plexiglass board which is marked off in tenths of inches. The readings of each crest (ridge) were recorded, and the average crest to crest distance was determined as follows:

$$\frac{\text{Sum of the Lengths of Each Crest}}{\text{Number of Crests}} = \text{Average Crest-to-Crest Distance}$$

The hair strands were then placed on a racking board and stretched and held in a straightened position for 24 hours at 100% humidity. Then, the strands were again placed on the plexiglass board and an average crest-to-crest measurement was determined. The percent relaxation was then determined as follows:

$$\frac{\text{Average Crest-to-Crest After Racking} - \text{Av. Crest-to-Crest Before Racking}}{\text{Average Crest-to-Crest Before Racking}} \times 100 = \% \text{ Relaxation}$$

In Table VII, the results of the "racking test" on these two lotion compositions show a very significant difference in relaxation.

TABLE VII

| | AVERAGE CREST-TO-CREST CHANGE (MEASURED IN INCHES) | | |
|---|---|---|---|
| | BEFORE RACKING | AFTER RACKING | PERCENT RELAXATION |
| Composition according to Present Invention (Table VI) | 0.8 | 0.85 | 6.25% |
| Prior Art Composition (Table V) | 0.8 | 0.9 | 12.5% |

EXAMPLE II

In order to further evaluate these two lotion compositions, half-head tests were conducted on live models. Half-head tests are performed on the hair by licensed beauticians on volunteer models.

In these tests, all procedures on the hair were identical, except for the application of one permanent wave lotion to the left side of the head and the application of the other lotion to the right side of the head.

Each head of hair was shampooed, wrapped with the same nmber and diameter of rods on each side, processed for the same length of time, water rinsed and neutralized with the same amount and composition of neutralizer. The beauticians evaluated the models immediately after the perm was finished and again four weeks later when the models returned for check-ups.

Crest-to-Crest curl measurements, in inches, were made at the front, crown and nape areas of the head and subjective evaluations were made for wet combing, elasticity and scalp wave. The subjective evaluations for these three characteristics were graded from Very Good, Good, Fairly Good, Fair, Poor and Very Poor. The average Crest-to-Crest measurements made initially and after four weeks were calculated as % relaxation by the following formula:

$$\frac{\text{Average Crest-to-Crest After 4 Weeks minus Av Crest-to-Crest Initially}}{\text{Average Crest-to-Crest Initially}} \times 100 = \% \text{ Relaxation}$$

The results of these six half-head tests are shown in Table VIII.

TABLE VIII

AVERAGE EVALUATIONS FOR 6 HALF-HEAD TESTS

| | % Relaxation After 4 Weeks | Wet Combing | Elasticity | Scalp Wave |
|---|---|---|---|---|
| Composition According to Present Invention (Table VI) | 10.1% | Very Good | Very Good | Very Good |
| Prior Art (Table V) | 13.7% | Fair | Fairly Good | Fairly Good |

Having described our invention, what we claim is new and desire to secure by Letters Patent is:

1. A permanent waving composition for providing longer lasting curl retention, manageability ease, and improved hair feel and appearance, said composition comprising, in addition to conventional permanent waving compounds formulated for breaking and re-bonding the hair fibers' disulfide bonds, the following additives:
   A. between about 0.001 and 2% by weight/volume of a strong hydrogen bonding amino acid compound
      a. formed from hydrolyzed silk protein, and
      b. having a mean molecular weight which enables the molecules to penetrate the cuticle in undamaged hair and enter the matrix in the cortex area of the hair fiber, and
   B. between about 0.001 and 2% by weight/volume of a water soluble or emulsifiable silicone-based compound.

2. The permanent waving composition defined in claim 1, wherein the hydrolyzed silk protein forming said strong hydrogen bonding amino acid compound is further defined as having a mean molecular weight of 90.

3. The permanent waving composition defined in claim 2 wherein said hydrolyzed silk protein amino acids are further defined as comprising glycine, alanine, serine and tyrosine.

4. The present waving composition defined in claim 1 wherein said water soluble or emulsifiable silicone based compound is further defined as comprising one selected from the group consisting of a polymer of dimethylsiloxane with polyoxyethylene and/or polyoxypropylene side chains and a polysiloxane polydimethyl dialkylammonium acetate copolymer.

5. The permanent waving composition defined in claim 1, wherein the silicone-based compound is further defined as comprising at least one selected from the group consisting of dimethicone, amodimethicone, stearoxytrimethylsilane, stearoxy dimethicone, and polysiloxane polyalkyl betaine copolymer.

6. A permanent waving composition for providing longer lasting curl retention, manageability ease and improved hair feel and appearance, said composition comprising:
   A. between about 2% and 10% by weight/volume of ammonium thioglycolate;
   B. between about 0.5 and 2% by weight/volume of a wetting agent;
   C. between about 0.001 and 2% by weight/volume of a silk protein hydrolyzed into its amino acids and having a molecular weight which enables the molecules to penetrate the cuticle in undamaged hair and enter the matrix in the cortex area of the hair fiber;
   D. between about 0.1 and 2% by weight/volume of a water soluble or emulsifiable silicone-based compound; and
   E. water forming the balance of the composition, with the final composition having its pH adjusted to between about 6 and 10.

7. The permanent waving composition defined in claim 5, further comprising:
   F. between about 2 and 10% by weight/volume of ammonium dithiodiglycolate.

8. The permanent waving composition defined in claim 6, wherein said pH is adjusted by employing one selected from the group consisting of alkanolamines, ammonia, and carbonates of ammonia.

9. The permanent waving composition defined in claim 6, wherein the amino acids of the hydrolyzed silk protein are further defined as comprising glycine, alanine, serine and tyrosine, and having a mean molecular weight of about 90.

10. The permanent waving composition defined in claim 6 wherein said water soluble or emulsifiable silicone based compound is further defined as comprising one selected from the group consisting of a polymer of dimethylsiloxane with polyoxyethylene and/or polyoxypropylene side chains and a polysiloxane polydimethyl dialkylammonium acetate copolymer.

11. The permanent waving composition defined in claim 6, wherein the silicone-based compound is further defined as comprising at least one selected from the group consisting of dimethicone, amodimethicone, stearoxytrimethylsilane, stearoxy dimethicone, and polysiloxane polyalkyl betaine copolymer.

12. A permanent waving composition for providing longer lasting curl retention, manageability ease, and improved hair feel and appearance, said composition comprising:
   A. between about 2 and 30% by weight/volume of glyceryl monothioglycolate;
   B. between about 0.5 and 2% by weight/volume of a wetting agent;
   C. between about 0.001 and 2% by weight/volume of silk protein hydrolyzed into its amino acids and having a molecular weight which enables the molecules to penetrate the cuticle in undamaged hair and enter the matrix in the cortex area of the hair fiber;

D. between about 0.001 and 2% by weight/volume of a water soluble or emulsifiable silicone based compound; and E. water forming the balance, with the pH of the final composition being adjusted to between about 6 and 8.5.

13. The permanent waving composition defined in claim 12 wherein said composition further comprises between about 2 and 30% by weight/volume of diglyceryl dithiodiglycolate.

14. The permanent waving composition defined in claim 12, wherein said pH is adjusted by employing one selected from the group consisting of alkanolamines, ammonia, and carbonates of ammonia.

15. The permanent waving composition defined in claim 12 wherein the amino acids of the hydrolyzed silk protein are further defined as comprising glycine, alanine, serine and tyrosine, and having a means molecular weight of about 90.

16. The permanent waving composition defined in claim 12 wherein said water soluble or emulsifiable silcone based compound is further defined as comprising one selected from the group consisting of a polymer of dimethylsiloxane with polyoxyethylene and/or polyoxypropylene side chains and a polysiloxane polydimethyl dialkylammonium acetate copolymer.

17. The permanent waving composition defined in claim 12, wherein the silicone-based compound is further defined as comprising at least one selected from the group consisting of dimethicone, amodimethicone, stearoxytrimethylsilane, stearoxy dimethicone, and polysiloxane polyalkyl betaine copolymer.

* * * * *